United States Patent
Vile et al.

(10) Patent No.: US 9,775,917 B2
(45) Date of Patent: Oct. 3, 2017

(54) NANOFIBRE AND BIOACTIVE COMPOSITIONS AND RELATED METHODS

(71) Applicant: ACTIVE FIBRES LIMITED, Blenheim (NZ)

(72) Inventors: Glenn Francis Vile, Blenheim (NZ); Iain Cameron Hosie, Auckland (NZ); Simon Vaughan Feasey, Auckland (NZ)

(73) Assignee: Active Fibres Limited, Blenheim (NZ)

( * ) Notice: Subject to any disclaimer, the term of this patent is extended or adjusted under 35 U.S.C. 154(b) by 0 days.

(21) Appl. No.: 14/774,365

(22) PCT Filed: Mar. 12, 2014

(86) PCT No.: PCT/NZ2014/000034
§ 371 (c)(1),
(2) Date: Sep. 10, 2015

(87) PCT Pub. No.: WO2014/142675
PCT Pub. Date: Sep. 18, 2014

(65) Prior Publication Data
US 2016/0038611 A1  Feb. 11, 2016

(30) Foreign Application Priority Data

Mar. 12, 2013 (NZ) ....................... 607760
Mar. 12, 2013 (NZ) ....................... 607762
Mar. 12, 2013 (NZ) ....................... 607763

(51) Int. Cl.
| | |
|---|---|
| A61F 13/00 | (2006.01) |
| A61K 47/48 | (2006.01) |
| A61C 19/00 | (2006.01) |
| A61K 8/97 | (2017.01) |
| D01D 5/00 | (2006.01) |
| D01F 1/10 | (2006.01) |
| A61K 8/49 | (2006.01) |
| A61K 8/65 | (2006.01) |
| A61K 8/66 | (2006.01) |
| A61K 8/81 | (2006.01) |
| A61C 19/08 | (2006.01) |
| A61K 8/98 | (2006.01) |
| A61K 8/02 | (2006.01) |
| A61K 35/644 | (2015.01) |
| A61K 36/185 | (2006.01) |
| A61K 36/73 | (2006.01) |
| A61K 36/87 | (2006.01) |
| A61C 19/02 | (2006.01) |
| B29C 65/76 | (2006.01) |
| A61K 9/70 | (2006.01) |
| A61K 9/00 | (2006.01) |

(52) U.S. Cl.
CPC ........ *A61K 47/48976* (2013.01); *A61C 19/00* (2013.01); *A61C 19/007* (2013.01); *A61C 19/02* (2013.01); *A61C 19/08* (2013.01); *A61K 8/0208* (2013.01); *A61K 8/498* (2013.01); *A61K 8/65* (2013.01); *A61K 8/66* (2013.01); *A61K 8/8129* (2013.01); *A61K 8/8135* (2013.01); *A61K 8/97* (2013.01); *A61K 8/988* (2013.01); *A61K 9/70* (2013.01); *A61K 35/644* (2013.01); *A61K 36/185* (2013.01); *A61K 36/73* (2013.01); *A61K 36/87* (2013.01); *B29C 65/76* (2013.01); *D01D 5/0038* (2013.01); *D01F 1/10* (2013.01); *D01F 1/103* (2013.01); *A61K 9/0092* (2013.01); *A61K 9/7061* (2013.01); *A61K 2800/413* (2013.01); *A61K 2800/57* (2013.01)

(58) Field of Classification Search
None
See application file for complete search history.

(56) References Cited

U.S. PATENT DOCUMENTS

| | | | |
|---|---|---|---|
| 7,569,359 B2 | 8/2009 | Mcdonnell et al. | |
| 7,732,427 B2 | 6/2010 | Kiick et al. | |
| 2005/0095695 A1* | 5/2005 | Shindler | B82Y 5/00 435/285.1 |
| 2006/0013869 A1 | 1/2006 | Ignatious et al. | |
| 2006/0083784 A1 | 4/2006 | Ignatious et al. | |
| 2009/0039565 A1 | 2/2009 | Reneker et al. | |
| 2010/0018641 A1 | 1/2010 | Branham et al. | |
| 2011/0129510 A1 | 6/2011 | Liebmann et al. | |
| 2012/0148493 A1 | 6/2012 | Schmehl et al. | |
| 2014/0083859 A1* | 3/2014 | Baeumner | B81B 1/006 204/601 |

FOREIGN PATENT DOCUMENTS

| | | |
|---|---|---|
| NZ | 501386 | 10/2002 |
| NZ | 519992 | 4/2004 |

(Continued)

OTHER PUBLICATIONS

International Search Report, International Application No. PCT/NZ2014/000034, dated Jun. 3, 2014, 4 pages.

(Continued)

*Primary Examiner* — Susan Tran
(74) *Attorney, Agent, or Firm* — Lathrop & Gage LLP

(57) ABSTRACT

Described herein are compositions in nanofiber form including one or more bioactive compounds releasably incorporated thereon. In one embodiment a composition is described comprising at least one nanofiber and at least one bioactive compound. The nanofibers are formed from a base material that is solubilized with the bioactive or bioactives in an aqueous based solvent solution and the base material and bioactives are together spun via electrospinning to form dry fibers with the bioactives chemically bonded to the nanofibers and the bioactives remaining stable during storage of the composition under ambient conditions substantially free of moisture. On exposure to moisture, the nanofibers dissolve, thereby releasing the bioactives.

25 Claims, 3 Drawing Sheets

(56) References Cited

FOREIGN PATENT DOCUMENTS

| WO | WO 01/38396 A1 | 5/2001 |
| WO | WO 01/54667 | 8/2001 |
| WO | WO 2008/149248 | 12/2008 |
| WO | WO 2013/035072 | 3/2013 |

OTHER PUBLICATIONS

International Written Opinion, International Application No. PCT/NZ2014/000034, dated Jun. 3, 2014, 8 pages.
First Examination Report dated Sep. 21, 2015, corresponding the New Zealand Patent Application No. 711906.
Yarin et al. (Apr. 2007), "Material encapsulation and transport in core-shell micro/nanofibers, polymer and carbon nanotubes and micro/nanochannels", J. Mater. Chem., 2007, 17, 2585-2599.
Abdel-Motaal et al., 2014, "*Biodegradation of poly (e-caprolactone) (PCL) film and foam plastic by Pseudozyma japonica sp. nov., a novel cutinolytic ustilaginomycetous yeast species*", 3 Biotech, 4:507-512.
Abedalwafa et al., 2013, "*Biodegradable Poly-Epsilon-Caprolactone (PCL) for Tissue Engineering Applications: A Review*", Rev. Adv. Mater. Sci. 34: 123-140.
Johnson et al., 2009, "*Electrospun PCL in Vitro: a Microstructural Basis for Mechanical Property Changes*", J. Biomaterials Science, Polymer Edition, 20: 467-481.
Witt et al., 2001, "*Biodegradation of aliphatic±aromatic copolyesters: evaluation of the final biodegradability and ecotoxicological impact of degradation intermediates*", Chemosphere, 44:289-299.

\* cited by examiner

NANOFIBRE AND BIOACTIVE COMPOSITIONS AND RELATED METHODS

CROSS-REFERENCE TO RELATED APPLICATIONS

This application is a U.S. National Stage Application under 35 USC §371 of International Application No. PCT/NZ2014/000034, filed Mar. 12, 2014, which claims the benefit of New Zealand Application Nos. 607760, 607762 and 607763, each filed Mar. 12, 2013. All of these applications are hereby incorporated by reference in their entireties.

TECHNICAL FIELD

Described herein are nanofibre and bioactive compositions and related methods. More specifically, compositions are described in nanofibre form including one or more bioactive compounds releasably incorporated thereon.

BACKGROUND ART

Delivery of bioactives is an issue spanning many art documents. A common theme is conversion of a bioactive or bioactives into a stabilised form so that the product may have a useful shelf life. A further consideration is that of incorporating the bioactive or bioactives into or onto a substrate that may be used to assist in delivery, for example to the skin of a patient.

The use of electro spinning to produce a nanofibre matrix that contains an active is known. See for example U.S. Pat. No. 7,732,427 and U.S. patent application Ser. No. 13/058,033 published as US 2011/0129510 on 2 Jun. 2011. However, there remains a need for active agent delivery systems that are particularly suitable for delivery to mammalian skin. One problem with art nanofibre and active agent combinations is that the active remains bonded to the nanofibre and is not quickly released on application.

Further aspects and advantages of the nanofibre and bioactive compositions and their usage will become apparent from the ensuing description that is given by way of example only.

SUMMARY

Described herein are compositions in nanofibre form including one or more bioactive compounds releasably incorporated thereon.

In a first aspect there is provided a composition comprising:
  at least one nanofibre; and
  an effective amount of at least one bioactive compound;
  wherein the nanofibres are formed from a base material that is solubilised with the bioactive or bioactives in an aqueous based solvent solution and the base material and bioactives are together spun via electrospinning to form dry fibres; and
  wherein the bioactives are chemically bonded to the nanofibres and the bioactives remain stable during storage of the composition under ambient conditions substantially free of moisture; and,
  on exposure to moisture, the nanofibres dissolve, thereby releasing the bioactives.

In a second aspect there is provided a multilayered matrix comprising a plurality of layers, each layer comprising the composition substantially as described above, wherein;

(a) the bioactives in at least one layer are segregated from bioactives in at least one other layer during storage preventing any reactions between the bioactives in each layer during storage; and, (b) on exposure to moisture, the nanofibres dissolve and the bioactives in the different layers mix and react together.

In a third aspect, there is provided a method of applying at least one bioactive compound topically to a subject to treat the skin of the subject, the method comprising the steps of:
  (a) selecting a composition substantially as described above;
  (b) moistening the composition;
  (c) applying the composition topically to the skin of the subject.

In a fourth aspect, there are provided cosmetic methods of treatment of a subject in need thereof by topical administration of the composition substantially as described above, the treatments selected from: promoting skin care or repair; assisting or enhancing wound healing; addressing a microbial infection; treating or preventing inflammation; promoting or enhancing cell proliferation; preserving or improving skin elasticity; preserving or improving skin moisture retention; lightening and/or whitening skin colour; delivering at least one antioxidant to skin; and combinations thereof.

In a fifth aspect, there is provided the use of a composition substantially as described above, in the manufacture of a medicament for treatments selected from: promoting skin care or repair; assisting or enhancing wound healing; addressing a microbial infection; treating or preventing inflammation; promoting or enhancing cell proliferation; preserving or improving skin elasticity; preserving or improving skin moisture retention; lightening and/or whitening skin colour; delivering at least one antioxidant to skin; and combinations thereof.

In a sixth aspect, there is provided a cosmetic skincare product comprising the composition substantially as described above, wherein the product is in the form of: a plaster, a bandage, a dressing, a facial mask, a facial strip, a cosmetic patch.

In a seventh aspect, there is provided a method of producing a composition substantially as described above by the steps of:
  (a) selecting at least one bioactive compound;
  (b) selecting at least one nanofibre base material;
  (c) mixing the bioactive compound or compounds and the nanofibre base material or materials with water to form an aqueous solution;
  (d) electro spinning the solution to form one or more nanofibres chemically bonded with the bioactive compound(s).

In an eighth aspect, there is provided a method of producing a multi-layer matrix substantially as described above by the steps of:
  (a) producing a first layer by the steps of:
    I. providing an active agent or agents;
    II. providing a nanofibre base material;
    III. mixing the active agent or agents and the nanofibre base material in a solvent phase to form a solution;
    IV. electro spinning the solution to form one or more nanofibres chemically bonded with the bioactive(s) in a first layer;
  (b) forming a second or further layer by separately repeating steps (I) to (IV) to form an additional layer;
  (c) combining the first and subsequent layers to form a multilayer composition.

As may be appreciated, the above aspects produce a product with bioactives stabilised and immobilised on nanofibres. Stabilisation of bioactives is important to ensure that they retain a useful shelf life and maintain full efficacy at eventual use. Further immobilisation of the bioactives/nanofibres on a substrate is also possible which places the bioactives in an immediately usable form e.g. a strip or dressing without further manufacture being necessary. In addition, the active or actives provide a known and repeatable dose unlike art active containing compositions such as creams where the active agent or agents may not be homogenous throughout the carrier substance. A further advantage is that the bond between the nanofibre and bioactives is strong in the absence of moisture hence useful for long term storage. On exposure to water, the nanofibres rapidly dissolve and release the bioactives. Similar art products do not release the bioactives in the same manner with art fibres creating irreversible bonds with the bioactives and not dissolving or only slowly dissolving thus not releasing the bioactive(s) in a timely or practical manner.

BRIEF DESCRIPTION OF THE DRAWINGS

Further aspects of the nanofibre and bioactive compositions and their usage will become apparent from the following description that is given by way of example only and with reference to the accompanying drawings in which.

DETAILED DESCRIPTION

Figure 1:
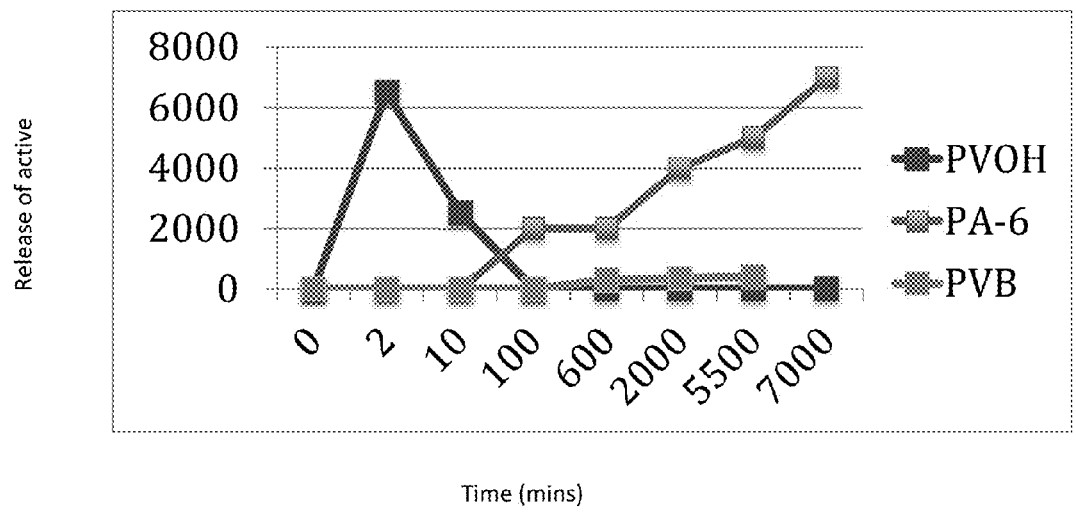
FIG. 1 is a graph showing the release of procyanidin B2 bioactive from a Vinanza™ skin performance plus extract incorporated into PVOH, PVB and PA-6 nanofibres.

As noted above, described herein are compositions in nanofibre form including one or more bioactive compounds releasably incorporated thereon.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term one or more active agents' or 'one or more bioactives' and grammatical variations thereof include analogues of active agents.

The terms 'bioactive' and 'agent' or grammatical variations may be used interchangeably for the purposes of this specification referring to a compound with an activity in vivo or in vitro that may be cosmetic or medical. Where the singular or plural of each word is used, the opposite may apply and use of the singular or plural for either term should not be seen as limiting.

The term 'analogues of active agents' or grammatical variations thereof refers to an active agent having a structure, function, and/or composition equivalent to that of the agent in a native or natural un-extracted form. Exemplary methods to determine functional equivalence of active agents, such as those obtained from plants and their analogues, are well known in the art and representative methods are provided herein in the Examples.

As used herein the term 'dressing' or grammatical variations thereof includes patches, strips, bandages or plasters.

As used herein the term 'promoting' or grammatical variations thereof includes initiating, enhancing or mediating, for example promoting a biological response includes initiating, enhancing or mediating a biological response.

The term 'effective amount' or grammatical variations thereof with reference to an amount or dosage of the composition described herein refers to an amount of a composition which is sufficient to effectively cause the described action such as preventing, treating or reducing a condition, the condition being a cosmetic change or medicinal change.

The term 'stable' or grammatical variations thereof refers to the active agent or agents not undergoing substantial physical changes, chemical changes, microbial growth, or any substantial loss in activity over time when stored in the absence of moisture.

The term 'natural' or 'natural based' and grammatical variations thereof refers to compounds obtained from nature or one or more synthesised versions of compounds found in nature. Ideally, the compound or compounds used meet the Natural Products Association (NPA) guidelines i.e. they are derived from renewable sources in nature' they do not use petroleum compounds, they meet generally recognised as safe or GRAS standard as set by the USA FDA and they are manufactured based on NPA approved processes.

The term 'phenolic compounds' and grammatical variations thereof refers to phenolic acids, phenolic salts, phenolic esters and related polyphenolic compounds incorporating one or more phenolic moieties.

The term 'dry' and grammatical variations thereof refers to a water activity sufficient to impair or stop microbial activity.

The term 'moisture' and grammatical variations thereof refers to the presence of a hydrating fluid such as water in sufficient amounts to at least support microbial growth.

The term 'dissolve' and grammatical variations thereof with reference to a solid such as a nanofibre, refers to the solid becoming a liquid or being incorporated into a liquid so as to form a solution.

In a first aspect there is provided a composition comprising:
at least one nanofibre; and
an effective amount of at least one bioactive compound;
wherein the nanofibres are formed from a base material that is solubilised with the bioactive or bioactives in an aqueous based solvent solution and the base material and bioactives are together spun via electrospinning to form dry fibres; and wherein the bioactives are chemically bonded to the nanofibres and the bioactives remain stable during storage of the composition under ambient conditions substantially free of moisture; and, on exposure to moisture, the nanofibres dissolve, thereby releasing the bioactives.

The inventors have identified a means to both stabilise bioactives on nanofibres through storage and have the bioactives release from the nanofibres in a controllable and repeatable manner.

Stability

The composition may be substantially stable over time in the absence of moisture. In one embodiment, the composition may be substantially stable for at least 7, or 14, or 21, or 28 days when stored at 20° C. in the absence of moisture. The composition may be substantially stable for at least 1, or 2, or 3, or 4, or 5, or 6, or 7, or 8, or 9, or 10, or 11, or 12 months when stored at 20° C. in the absence of moisture. Based on the inventor's experience, the anticipated stability when stored at typical ambient conditions (15 to 30° C.) may be greater than 1 year. The composition may be stable for at least 28 days at 45° C. and 95% relative humidity.

As noted above, the composition is substantially stable post spinning.

Also as noted above, important in maintaining stability is the absence of moisture. The term 'absence of moisture' may refer to a water activity less than approximately 0.7. The term 'absence of moisture' may instead refer to a relative humidity less than approximately 80%, or 70%, or 60%, or 50%, or 40%, or 30%, or 20%. As should be appreciated, it is relatively simple to achieve such absence of moisture by packaging the composition in sealed package. Post spinning, the water activity is also well below 0.7 hence shorter term storage may not even require completely sealed packaging. Also as noted above, the composition does not require any special temperature storage conditions and may be stored at ambient temperatures avoiding the need for extra energy requirements such as refrigeration.

The above characteristic makes the composition excellent for storage of active compounds that can be prone to loosing their activity over time. The above characteristic also makes it simple to release the bioactives since a simple action such as dipping or wetting the composition in or with water will release the bioactives through dissolution of the nanofibres.

Bonding

As noted above, the bioactives once spun are chemically bonded to the nanofibres and remain stable when stored over time. It is understood by the inventors that the stability at least in part is due to the strong chemical bonds that are formed between the bioactive compound(s) and the nanofibres. The bonds may be covalent bonds. Covalent bonds are known to be particularly strong and stable bonds. Because the actives site or sites on the bioactives are bound covalently to the nanofibres, the bioactives are thereby rendered inactive while bonded. This ensures that the bioactives are effectively preserved over time pending dissolution of the nanofibres. When dissolution occurs, as will be described further below, the bioactive compounds are then 're-activated'—in other words, the chemical bonding is reversible.

The inventors have found that, unlike art compositions, the bonding in the compositions described above is reversible—in other words, the bond is permanent to semi-permanent in the absence of moisture, however, on exposure of the nanofibres to moisture, the bond rapidly disappears and release of the bioactives occurs. Art fibres either do not dissolve or only dissolve slowly thus not releasing the bioactives quickly to the site of administration.

Bioactives

The bioactives may be selected from: compounds that have at least one phenolic moiety; enzymes including a polypeptide with one or more tyrosine residues; and combinations thereof Bioactive compounds that may include one or more phenolic moieties and which may be used may be selected from: one or more benzoic acids, such as gallic acid, syringic acid, vanillic acid, one or more hydroxycinnamic acids, including caffeic acid, caftaric acid, GRP, p-coumaric acid, coutaric acid, one or more flavan-3-ols, such as catechin, epicatechin, one or more stilbenes, including t-resveratrol, and t-piceid, one or more flavanols, including quercetin, myricetin and rutin, and one or more anthocyanins, including delphinidin, petunidin, cyanidin, malvidin and peonidin. The active agent or agents may further include: phenyllactic acid, methoxylated phenyllactic acid, methoxylated benzoic acids, syringic acid, methyl syringate, isomeric forms of methyl syringate, and combinations thereof.

As noted above, the bioactive may also be an enzyme. The enzyme may be selected from: myrosinase, peroxidase, glucose oxidase, royalisin, apalbumin, apisimin, actinidin, papain, bromelain, quinone oxidoreductase, glutathione S-transferase, tyrosinase, and myeloperoxidase.

The bioactives may also include polypeptide, peptide or peptide fragmented cellular matter such as cell wall fragments. The cellular matter may be from a plant or animal.

The bioactives may be directly extracted from a plant or plant part. The active agent or agents may alternatively be extracted from a natural based product that includes at least in part, compounds derived from a plant or part thereof. The above sources include bioactives or chemicals isolated from plants, and their analogues. Plants contain a range of bioactive compounds, for example, compounds that protect the plants from environmental stress such as UV radiation and microbial contamination. Such compounds may be useful in human health or animal health.

Examples of direct sources of useful bioactives may include but are not limited to: grape seed, kiwifruit, blackcurrant, boysenberries, red grape, broccoli, broccoli sprout, olive leaf, aloe, ginger, olive or olive leaf, ginseng, seaweed, pine bark, as well as essential oils and extracts of the bioactives from these oils.

Examples of naturally made products that include plant-derived bioactives may include honey, propolis, royal jelly, and combinations thereof. As may be appreciated, these products include bioactives derived from plant materials as well as further including other materials and potentially bioactive compounds from other sources. An example of another potentially useful bioactive in honey is the compound arabinogallactan (AG) isolated or bound to a protein that may also associate with or bond to the nanofibres. Specific examples of honey products that fall into this group include: manuka honey, kanuka honey, rewarewa honey.

By way of example, bioactives having antioxidant activity may be obtained from one or more of grapes, boysenberries, blackcurrants and kiwifruit. Bioactives having anti-inflammatory and antioxidant activity may be obtained from grapes. Bioactives having antioxidant and anti-bacterial activity can be obtained from grape and blackcurrant. Bioactives having medical applications may be extracted from honey.

In some embodiments the bioactives in a raw material may be extracted using solvent extraction prior to mixing with the nanofibre. The solvent may be water or ethanol.

In the case of honey for example, the saccharide portion of the honey may be removed to provide a bioactive extract used in the composition described above. One advantage of the above composition is that the inherent stickiness or tackiness and running nature of honey may be removed by extraction and incorporation into the nanofibres described herein. The result may be a very simple to use composition without many of the complications of using pure honey itself particularly for topical administration. A further advantage of the composition, at least in respect of honey, may be that the chemical composition of honey changes over time, one change being the measurable levels of phenolic compounds. When producing medical compositions, changes in activity over time are not desirable hence, a method such as that described to stabilise such compounds may be highly desirable.

It should be appreciated that the bioactives may be present with the nanofibre or nanofibres or in the nanofibre matrix at a concentration or amount sufficient to provide an effective amount of bioactive(s) to the surface to which the nanofibre or nanofibres are applied. For example, in certain embodiments the one or more bioactives may be present in the nanofibre or nanofibres at a concentration or amount sufficient to provide an effective dose of bioactive(s) to a skin surface on which the nanofibre or nanofibres are applied.

Dosage and known dosage amount is in fact a key advantage of the compositions described herein. With other bioactive delivery systems such as creams and ointments, the actives may become segregated from the carrier or not be dispersed uniformly throughout the carrier. In the present case, the bioactive or actives can be bonded to the nanofibres in a known quantity and this amount does not alter over time meaning the dose on application may be known and repeatable over a production run and after storage.

The loading of the active agent or agents on the nanofibre or nanofibres may be about 0.1, 0.5, 1, 1.5, 2, 2.5, 3, 3.5, 4, 4.5, 5, 10, 15, 20, 25 or 30 g/m². The loading may be about 0.1 to 30 g/m².

The active agent or agents may consist of about 10, 15, 20, 25, 30, 35, 40, 45, 50, 55, 60, 65, 70, 75 or 80% by weight of the composition. The active agent or agents may consist of about 10 to 80% by weight of the composition.

Nanofibres

The nanofibre or nanofibres may in one embodiment be manufactured from a polymer selected from: polyvinyl alcohol (PVOH), polyvinyl alcohol (PVA), polyamide 6 (PA-6), polyvinyl butyral (PVB), polyamide 6,6 (PA-6,6), polyethylene terephthalate (PET), polybutylene terephthalate (PBT), polylactic acid (PLA), poly(lactic-co-glycolic) acid (PLGA), polycaprolactone (PCL), nylon, alginate, cellulose, cellulose derivatives including cellulose acetate and carboxymethyl cellulose (CMC), gelatine, gelatin, chitosan, carrageenan, xanthan gum, zein, polysaccharides generally, polyhydroxyalkanoates (PHA), polyhydroxybutyrate (PHB), poly(3-hydroxybutyrate-co-3-hydroxyvalerate) (PHBV), and combinations thereof.

In an alternative embodiment, the nanofibre or nanofibres may be formed from collagen protein. The collagen protein may in one embodiment be marine derived. The marine derived collagen may be sourced from cold water fish, such as hoki (*Macruronus novaezelandiae*). Marine derived collagen has certain advantageous properties such as a lower gelling temperature. Marine sources and in particular hoki also has the advantage of having a low amino acid (proline and hydroxyproline) content (147 residues/1000 residues) compared to collagen from the skin of calf (*Bos taurus*) (232/1000) and that from the temperate fish, carp (*Cyprinus carpio*) (197/1000). Amino acids give rigidity to the α-chain helix. Therefore, the low amino acid content helps to break down the helix into alpha chains (denatured whole chain) which are more suitable for electrospinning compared to native collagen, atelocollagen and gelatin.

A further advantage of collagen as the nanofibre is the ability to source the material naturally. From a marketing perspective, synthetic sources such as non-natural polymers may be less appealing to a consumer than a natural based collagen nanofibre.

The collagen protein may be denatured prior to spinning. The denaturing process converts the collagen to remove its helical structure and form whole chains (alpha chains). Denaturing refers to disrupting the protein helix structure. In denaturing the protein, the normally present two actives sites for bonding can be increased 2-fold, or 3-fold, or 4-fold, or 5-fold, or 6-fold—in other words, denaturing the protein dramatically increases the ability to load the nanofibres with bioactives and thereby improves the loading rate of bioactives. Denaturing may occur when the solvent solution is prepared, for example by reducing the solution pH by the addition of an organic acid or alcohol. For example, a cosmetic patch can be smaller for the same concentration of bioactives as a comparable native state collagen protein. The inventors also found that, by denaturing the collagen, the resulting solvent solution including the denatured collagen was easier to electrospin. Electrospinning native collagen is difficult while the denatured form is unexpectedly easier to electrospin. As may be appreciated, denaturing as described above differs to that generally referred to in the art being hydrolysing or altelocollagen, processes that do not have the same effect of increasing the number of active sites.

The collagen nanofibre material may include at least one polypeptide with one or more tyrosine residues. The inventors found that, at least in the case of phenolic compounds, the phenol groups of the bioactives where present, have a high chemical affinity towards the amino acid residues such as the tyrosine residues.

The nanofibre may be formed as a homogenous nanofibre or as a heterogeneous nanofibre. A homogenous nanofibre is one in which the nanofibre is formed from a single polymer/protein. e.g. collagen. A heterogeneous nanofibre is one in which the nanofibre is formed from two or more polymers/proteins, for example collagen protein and PVOH polymers.

When formed as a multi-polymer nanofibre, fibres formed from one polymer/protein may associate together, for example using van der waals forces, and the second polymer/protein may be associated with the first polymer/protein. For example, in one case of a nanofibre formed from collagen and PVOH, the collagen forms a fibre where the collagen nanofibres are associated with each other by van der waals forces and the PVOH nanofibres forms an associated polymer.

In some embodiments, nanofibres may be formed into a matrix of nanofibres. The matrix may be woven or non-woven.

The diameter of the nanofibre may be about 10, 50, 100, 150, 200, 250, 300, 350, 400, 450, 500, 550, 600, 650, 700, 750, 800, 850, 900, 950, 1000 nm and useful ranges may be selected between any of these values (for example, from about 10 to about 1000, about 10 to about 900, about 10 to about 750, about 10 to about 600, about 10 to about 500, about 10 to about 300, about 10 to about 100, about 100 to about 1000, about 100 to about 950, about 100 to about 800, about 100 to about 600, about 100 to about 500, about 100 to about 350, about 250 to about 1000, about 250 to about 900, about 250 to about 850, about 250 to about 750, about 250 to about 550, about 250 to about 500, about 250 to about 400, about 300 to about 1000, about 300 to about 750, about 300 to about 600, about 300 to about 400, about 400 to about 1000, about 400 to about 900, about 400 to about 700, about 400 to about 600, about 400 to about 500, about 500 to about 1000, about 500 to about 750, about 500 to about 600, about 650 to about 1000, about 650 to about 900, about 650 to about 750, about 700 to about 1000 or about 800 to about 1000 nm). Nano size fibres are of importance as they ensure the greatest possible surface area on which active agents may associate with and/or bond. The small size also allow faster dissolution on exposure to moisture, in turn causing faster release of the bioactives.

Electrospinning Solution

As may be appreciated, a key aspect of forming the desired nanofibre and bioactive combination is in achieving the optimum solvent solution. Art documents teach about use of many different chemicals as electrospin solvents and enhancers however many of these compounds are non-natural and can be expensive and/or hard to source and handle. As described, an aqueous or water based solution is used in the preparation of the above solvent solution. The combination of water, nanofibre base material and bioactives may all that is used to form the solution. In one embodiment, the solvent solution may further comprise at least one organic acid compound and/or at least one alcohol compound. The organic acid and/or alcohol may be relatively weak. The organic acid may be selected from: citric acid, acetic acid, formic acid, carbonic acid, and combinations thereof. The alcohol may be selected from: ethanol, benzyl alcohol, isopropanol, and combinations thereof. The organic acid and/or alcohol may comprise less than approximately 20% of the solvent solution.

An aim of including the above described compounds may be to adjust the solution conductivity, surface tension and viscosity of the solution to optimise the subsequent electrospinning process. As may be appreciated, the organic acids and alcohols used are relatively benign and often natural in origin. No further agents may be added to the solvent solution in order to achieve the spun nanofibre and bioactive(s) composition. By way of illustration, the conductivity of the solution may be approximately 1, or 2, or 3, or 4, or 5 mS/cm or from 1 to 5 mS/cm. The surface tension of the solution may be approximately 50, or 100, or 150, or 200, or 250, or 300, or 350, or 400, or 450, or 500 mN/m or 50-500 mN/m. The viscosity of the solution may be approximately 250, or 500, or 750, or 1000, or 1250, or 1500, or 1750, or 2000 cSt or 250 to 2000 cSt. The above ranges are provided by way of illustration only and, as should be appreciated, may be varied to suit the chosen nanofibre material, bioactive(s) and any other agents or compounds used (if any). The above described compounds may also be useful in that they can denature the protein structure of a collagen protein in a manner that increases the number of active sites.

In one embodiment, the only compounds used to make the solvent solution are the nanofibre polymer or protein, the bioactives, water and optionally at least one organic acid and/or an alcohol. Through careful selection as noted above, the inventors have managed to minimise the number of compounds needed to form an optimum electrospinning solution. In addition, all of the compounds used may be of a natural origin if desired.

Layering on Application

In some embodiments, on application to skin, the dissolved nanofibre may form a cover layer over the application site as the dissolved nanofibre material dries. As used herein, the term 'cover layer' refers to the dissolved fibre forming a layer that covers the skin site reducing exposure of the skin site to the environment either in a semi-permeable manner or in an impermeable manner.

Solubility and Dissolution

As noted above, the nanofibres described herein dissolve in the presence of moisture. In one embodiment, the nanofibres dissolve and release substantially all of the bioactives within about 5 minutes when moistened. The dissolution rate may be a rate of at least 0.1 mg/min when solubilised in water at a temperature of 15-30° C.

Dissolution, particularly at the rapid rate noted represents a significant change to the art where for example irreversible covalent bonding occurs. In the art, bioactives if present are typically only released from a fibre matrix in a slow manner or even not at all. The inventors have found that by use of high surface area nanofibres, the fibres dissolve rapidly in the presence of moisture and release any actives associated with or bound to the nanofibres.

The nanofibres may be tailored to release substantially all of one or more of the active agents to which it is associated or bound within about 5 minutes, within about 4 minutes, within about 3 minutes, within about 2 minutes, within about 110 s, within about 100 s, or within about 60 seconds, when applied to skin.

The temperature of solubility may range from 15, or 16, or 17, or 18, or 19, or 20, or 21, or 22, or 23, or 24, or 25, or 26, or 27, or 28, or 29, or 30° C. As noted above, the rapid speed of dissolution may occur on skin and at skin temperatures of around 15-30° C. Topical delivery is a preferred application hence the composition must be designed to maximise delivery or dissolution at skin temperatures. Typically higher temperatures promote faster dissolution however, in the present case, temperatures above 30° C. are undesirable due to the unpleasant effect of higher temperatures on the skin as well as the need to then heat the composition prior to use.

Substrate

In some embodiments the nanofibre, nanofibres or matrix of nanofibres may be spun onto a substrate or support. The support may be formed from woven material such as cloth, or non-woven material such as plastic. Some specific examples of support or substrate include vilene, nylon, viscose, cotton, polypropylene in the form of gauze, mesh, non-woven or woven textile. An aim of the substrate may be to give the nanofibres more structural strength as may be needed for the end product of the composition such as for a patch.

Layers

In a second aspect there is provided a multilayered matrix comprising a plurality of layers, each layer comprising the composition substantially as described above, wherein;

(a) the bioactives in at least one layer are segregated from bioactives in at least one other layer during storage preventing any reactions between the bioactives in each layer during storage; and, (b) on exposure to moisture, the nanofibres dissolve and the bioactives in the different layers mix and react together.

In the above embodiment, at least one layer is made from a nanofibre material that dissolves at a different rate to a second or further layer, thereby releasing the bioactive(s) at different rates.

As may be appreciated, segregating bioactives in a single delivery vehicle may be advantageous as it avoids the bioactives reacting together during storage yet allows co-administration, avoiding the need to apply two different products. At least from a convenience point of view, providing one product that delivers multiple bioactives would be of benefit particularly if the bioactives were normally incompatible.

The first nanofibre and the at least one further nanofibre may be the same material. Alternatively, the first nanofibre may differ to at least one or more of the nanofibres used in the further layer or layers. By way of example, a multilayered matrix may be formed from a first layer made from PVOH nanofibres bonded with a first bioactive, and a second layer of the matrix, formed from PA-6 nanofibre, with a different bioactive bonded thereon.

The nanofibres in each layer may form a homogenous or heterogeneous matrix of nanofibres. A homogenous matrix of nanofibres is one in which the matrix layer or layers may be formed from a single nanofibre. A heterogeneous matrix of nanofibres is one in which the matrix is formed from multiple different nanofibres.

Nanofibres formed from one polymer or protein may be associated together, for example using van der waals forces, to form a layer, and nanofibres formed from a different polymer or protein may be associated together to form another layer. Each layer may be associated with the other, for example by van der waals forces. For example, in one case of a multilayer nanofibre matrix formed from collagen and PVOH, the collagen nanofibres form a layer where the collagen nanofibres are associated with each other, for example by van der waals forces, and the PVOH nanofibres form an associated layer.

As noted above, the nanofibre material may be varied to dictate the rate of release of the active. Polymers and proteins may dissolve at varying rates. In one embodiment, the first layer may be made from a nanofibre that releases a bioactive at a first speed while a second layer may release a second bioactive at a second speed. The second speed may be slower than the first speed. The second speed may be faster than the first speed. One example of this application may be in delivery of a bioactive compound that requires activation or catalysation via an enzyme. The first layer dissolves rapidly to release inactive bioactive on to skin and then, at a slower rate, the second layer of nanofibre dissolves releasing an active enzyme that catalyses conversion of the inactive bioactive to an active state. As may be appreciated, a multi-layer composition as described may be helpful as it ensures conversion of the inactive bioactive and does this at the actual site where the bioactive is needed (for example, the skin). This means minimal loss in activity hence a known and repeatable dosage.

It should be appreciated that the targeted selection of bioactive and nanofibre enables the production of a multi-layer nanofibre matrix having multiple kinetics of bioactive release, for example wherein one or more bioactives may be rapidly released from one nanofibre present in the matrix, such as to give an antibacterial or antimicrobial effect, and one or more bioactives may be released over a longer period, for example to support skin repair, recruit immune cells to the site of application, or the like.

Methods of Use and Treatments

In a third aspect, there is provided a method of applying at least one bioactive compound topically to a subject to treat the skin of the subject, the method comprising the steps of:
(a) selecting a composition substantially as hereinbefore described;
(b) moistening the composition;
(c) applying the composition topically to the skin of the subject.

In a fourth aspect, there are provided cosmetic methods of treatment of a subject in need thereof by topical administration of the composition substantially as described above, the treatments selected from: promoting skin care or repair; assisting or enhancing wound healing; addressing a microbial infection; treating or preventing inflammation; promoting or enhancing cell proliferation; preserving or improving skin elasticity; preserving or improving skin moisture retention; lightening and/or whitening skin colour; delivering at least one antioxidant to skin; and combinations thereof.

In a fifth aspect, there is provided the use of a composition substantially as described above, in the manufacture of a medicament for treatments selected from: promoting skin care or repair; assisting or enhancing wound healing; addressing a microbial infection; treating or preventing inflammation; promoting or enhancing cell proliferation; preserving or improving skin elasticity; preserving or improving skin moisture retention; lightening and/or whitening skin colour; delivering at least one antioxidant to skin; and combinations thereof.

As noted above, the composition may be used in a variety of different ways. Applications envisaged by the inventors include (but are not limited to): cosmetic topical treatments such as promoting skin care or cosmetic repair, promoting or enhancing cell proliferation in skin, preserving or improving skin elasticity, preserving or improving skin moisture retention; or lightening and/or whitening skin colour; or delivering at least one antioxidant to skin; or combinations of the above treatments.

The compositions may also be used for a variety of medical treatments. Examples of such use include (but are not limited to): promoting skin care or repair; or assisting or enhancing wound healing; or addressing a microbial infection; or treating or preventing inflammation; or promoting or enhancing cell proliferation delivering at least one antioxidant to skin; or combinations of the above treatments.

The subject as described above may be a human. The subject may also be a non-human. Human use for both cosmetic and medical treatments is envisaged since the composition may be sterilised, may be simple to use, and may be used for a wide variety of end products. Non-human applications may include faster ways to deliver active agents to livestock—for example, when a horse is wounded a dressing may be applied and an antiseptic cream administered under the dressing. Using the above composition, the nanofibres may include antibacterial and anti-inflammatory bioactives on the nanofibres all loaded onto a dressing substrate eliminating the need for a cream application. Environmental moisture such as humidity and sweat as well as any exudate may be sufficient to cause the nanofibres to dissolve and release the bioactives. Non-human animals may include horses, cattle, sheep, goats, and companion animals such as dogs and cats.

It should be appreciated that the composition may be used for a wide variety of treatments, the treatment choice being at least in part based on what bioactives are incorporated into the composition. The stability of the bioactives during storage and rapid release on application of the composition may be highly desirable attributes in at least the applications noted above.

SPECIFIC EMBODIMENTS

As noted above, the composition broadly relates to the combination of nanofibres and one or more bioactives chemically bonded to the nanofibre where the nanofibres dissolve and release the bioactives on exposure to moisture.

One key embodiment may be as a cosmetic product.

In a sixth aspect, there is provided a cosmetic skincare product comprising the composition substantially as described above, wherein the product is in the form of: a plaster, a bandage, a dressing, a facial mask, a facial strip, a cosmetic patch.

As noted above, in one embodiment, the composition may be a mixture of collagen nanofibres and bioactives. This combination may have a dual treatment effect for cosmetic applications. Collagen is well known to have a fast acting moisturising effect that address skin wrinkles. The bioactives used may have a long acting skin wrinkle action. The combination product may then be used as a skin wrinkle treatment that has both immediate effects and more long lasting effects.

In another embodiment, the composition may include one or more nanofibres formed from cold water fish collagen and additionally including about 10 to about 80% by weight of an active agent, and wherein the diameter of the fibres may be between about 10 to about 1000 nm.

In another embodiment, the composition includes one or more nanofibres formed from cold water fish collagen and additionally including about 10 to about 80% by weight of an active agent, and wherein the rate of solubility of the nanofibres in water at a temperature of about 15-30° C. is at least 0.1 mg/min.

As noted above, the composition may be formulated for topical delivery including for use in cosmetic applications as well as for use in medical treatments.

As noted above, the composition including the nanofibre or nanofibres and active(s) may be retained onto a support or substrate. The support or substrate may be formed from plastic or cloth. For example, the backing may be formed from polypropylene sheets. It should be appreciated that any suitable inert backing support could be used. Suitability can be dependent on the support or substrate compatibility with skin (i.e. non-toxic) and the ability to carry the nanofibres without any significant loss of the nanofibres from the support or substrate. In some embodiments the nanofibre or nanofibres may be applied to a support and used as a plaster, bandage, dressing, operating gown, facial mask, facial strip, or cosmetic patch.

In one particular embodiment, the composition including the nanofibre(s) and active(s) may be retained within two opposing inert layers keeping the composition substantially moisture free during storage. On use, one of the layers may be removed exposing the composition nanofibre and active layer. The composition may be moistened, for example by dipping the composition and remaining layer in water, or by applying water to the skin surface and then the composition may be applied to the skin surface with the nanofibre and actives directly touching the skin surface. The layer may then be removed post application. The act of pressing the composition against the skin transfers the active(s) to the skin surface and, due to the rapid dissolution of the nanofibres, the actives are free to transfer i.e. no longer associated or chemically bound to the nanofibres. Application times may be as short as a matter of seconds to effect transfer. The layered approach as described above may be in strips, in sheets or in contoured shapes to suit a body feature such as the face.

Sterilisation

The above described composition may be sterilised to meet medical requirements yet the bioactives retain their efficacy.

In one embodiment, sterilisation is completed using irradiation. A sterilisation effective dose may be greater than 10 kGy. In one embodiment the dose may be greater than 20 kGy. In a further embodiment, the dose may be greater than 30 kGy. In a yet further embodiment, the dose may be 32.5 kGy to 60 kGy. Some art compositions become unstable and separate post irradiation treatment hence stability despite irradiation is an advantage over the art. Irradiation is important in many applications such as medical applications to ensure that there are no residual microbes that may cause infection of a wound.

Manufacture

In a seventh aspect, there is provided a method of producing a composition substantially as described above by the steps of:

(a) selecting at least one bioactive compound;
(b) selecting at least one nanofibre base material;
(c) mixing the bioactive compound or compounds and the nanofibre base material or materials with water to form an aqueous solution;
(d) electro spinning the solution to form one or more nanofibres chemically bonded with the bioactive compound(s).

In an eighth aspect, there is provided a method of producing a multi-layer matrix substantially as described above by the steps of:

(a) producing a first layer by the steps of:
   I. providing an active agent or agents;
   II. providing a nanofibre base material;
   III. mixing the active agent or agents and the nanofibre base material in a solvent phase to form a solution;
   IV. electro spinning the solution to form one or more nanofibres chemically bonded with the bioactives in a first layer;
(b) forming a second or further layer by separately repeating steps (I) to (IV) to form an additional layer;
(c) combining the first and subsequent layers to form a multilayer composition.

The solvent used in step (c) may be any suitable solvent providing the solvent does not leave a toxic residue, solubilises both the polymer and the bioactives, does not inactive the bioactives in a permanent manner, and evaporates off during electro spinning. Selected solvents may also assist in the formation of the one or more nanofibres.

In some embodiments only a single polymer/protein may be used. For example, collagen protein may be used to produce a homogenous nanofibre. Alternately, other polymers/proteins may be incorporated into the solvent substantially as described above. The composition may be spun directly onto a support or substrate.

The resulting composition may be applied to a support or substrate post electro-spinning for final applications such as those described above.

As noted above, a key aspect of the manufacturing process may be in choice of nanofibre material and optimising the key electrospinning parameters in order to allow for the bioactive(s). As noted above, key parameters include optimising the solvent solution, particularly in terms of conductivity, surface tension and viscosity.

In summary, the above described composition and other aspects have many advantages over the art including supply of active agents stabilised and immobilised on a substrate. Stabilisation of bioactives is important to ensure that they retain a useful shelf life and maintain full efficacy at eventual use. Immobilisation on a substrate is useful as this places the active in an immediately usable form e.g. a strip or dressing without further manufacture being necessary. In addition, the active or actives provide a known and repeatable dose unlike art active containing compositions such as creams where the bioactives may not be homogenous throughout the carrier substance. A further advantage is that the bond between the substrate and active is strong in the absence of moisture hence, useful for long term storage, but, on exposure to water, the substrate rapidly dissolve and release the bioactives. Similar art products do not release the bioactives in the same manner.

The embodiments described above may also be said broadly to consist in the parts, elements and features referred to or indicated in the specification of the application, individually or collectively, and any or all combinations of any two or more said parts, elements or features, and where specific integers are mentioned herein which have known equivalents in the art to which the embodiments relates, such known equivalents are deemed to be incorporated herein as of individually set forth, Where specific integers are mentioned herein which have known equivalents in the art to which this invention relates, such known equivalents are deemed to be incorporated herein as if individually set forth.

WORKING EXAMPLES

The above described nanofibre and bioactive compositions and their usage are now described by reference to specific examples.

Example 1: Wound Healing Matrix

This example describes the use of a skin patch for assisting or enhancing wound healing.

As a first step the active agent is obtained. The active agent is a plant extract and is obtained from one or more of grapes, boysenberries, blackcurrants and kiwifruit using water extraction. The active agent includes bioactives that have a phenolic moiety.

The next step is to obtain the polymer user for the formation of the nanofibres. In this particular example the polymer is collagen obtained from Hoki, a cold water fish, using the process as described in New Zealand patent 501386, published as PCT international patent application WO 2001/038396A1.

The active agent and the collagen protein are then mixed in a solvent phase comprising water and acetic acid. It should be appreciated that any suitable solvent can be used providing it does not leave a toxic residue, solubilises both the polymer and the active agent, does not inactive the active agent, and evaporates off during electro spinning. This solvent phase is also useful in that it denatures the collagen protein.

Once prepared the polymer-active agent solution is electrospun. The electrospinning produces a matrix of nanofibres.

The matrix of nanofibres is then applied directly to a support, such as a woven support or a plastic patch. The resulting product at this point includes stabilised active agents. When ready for use, the support or plastic patch is then applied to a wound, with the facing of the patch containing the nanofibres being applied to the skin.

The nanofibres solubilise quickly delivering the active agent(s) and the collagen to the wound.

Example 2: Skin Repair

This example describes the use of a skin patch for assisting or enhancing skin repair.

As a first step the active agent actinidin is provided from kiwifruit (*Actinidia deliciosa*) using water extraction.

The next step is to provide the polymer user for the formation of the nanofibres. In this particular example the polymer is marine collagen obtained from Hoki, a cold water fish, using the process as described in New Zealand patent 501386, published as PCT international patent application WO 2001/038396A1.

The active agent and the collagen polymer are then mixed in a solvent phase comprising water and acetic acid.

Once prepared the polymer-active agent solution is electrospun. The electrospinning produces a matrix of nanofibres.

The matrix of nanofibres is then applied directly to a support, such as a woven support or a plastic patch.

The support or plastic patch is then applied to the skin, with the facing of the patch containing the nanofibres being applied to the skin.

The nanofibres solubilise quickly delivering the actinidin and the collagen to the skin.

Example 3: Bioactive Dressing/Patch

This example analyses the efficacy of a dressing or patch that contained bioactive extracts that have skin repair and skin care functions. The bioactives were contained within a layer or layers of nanofibres that dissolved or released the actives at different rates.

The active agent in this example comes from plant sources that include grapes, berries, kiwifruit and other plant material. The plant extract contained concentrated levels of bioactives including carotenoids, phenolics and enzymes.

Three different matrices of nanofibres were used.

A matrix was formed from either PVOH, or PVB or PA-6 nanofibres impregnated with Vinanza™ Skin Performance Plus Extract as obtained from New Zealand Extracts™ Limited.

The nanofibres were spun to form layers of nanofibres on polypropylene sheets.

The sheets were then incubated in Hanks solution and the release of the bioactives was measured over time.

The different nanofibre materials released the bioactives at different rates. For example, phenolic bioactives were released from PVOH nanofibres within two minutes whereas with PA-6 nanofibres the bioactives were released from the fibres over several days. PVB showed an even longer release time period.

By way of illustration, FIG. 1 illustrates the release of procyanidin B2 bioactive from the nanofibre matrix impregnated with Vinanza™ Skin Performance Plus Extract. Procyanidin B2 is chosen as a marker compound given it is a key skin treatment bioactive. As can be seen in FIG. 1, the nanofibre formed from PVOH released the phenolic bioactive effectively instantly, the nanofibre formed from PA-6 released the phenolic over a much longer period of time, and the PVB nanofibre was only just starting to release bioactive at the conclusion of the trial time period.

Figure 2:
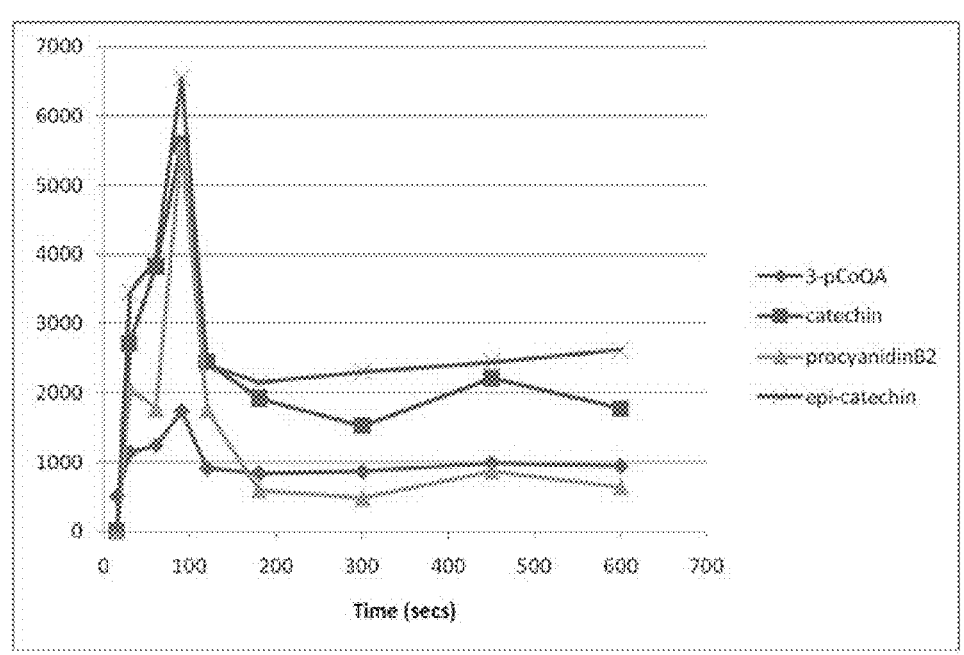
FIG. 2 is a graph showing the release of individual phenolic active agents 3-pCoQA (♦), catechin (■), procyanidinB2 (▲), and epi-catechin (X) from the PVOH nanofibre matrix as described in Example 3.
Figure 3:
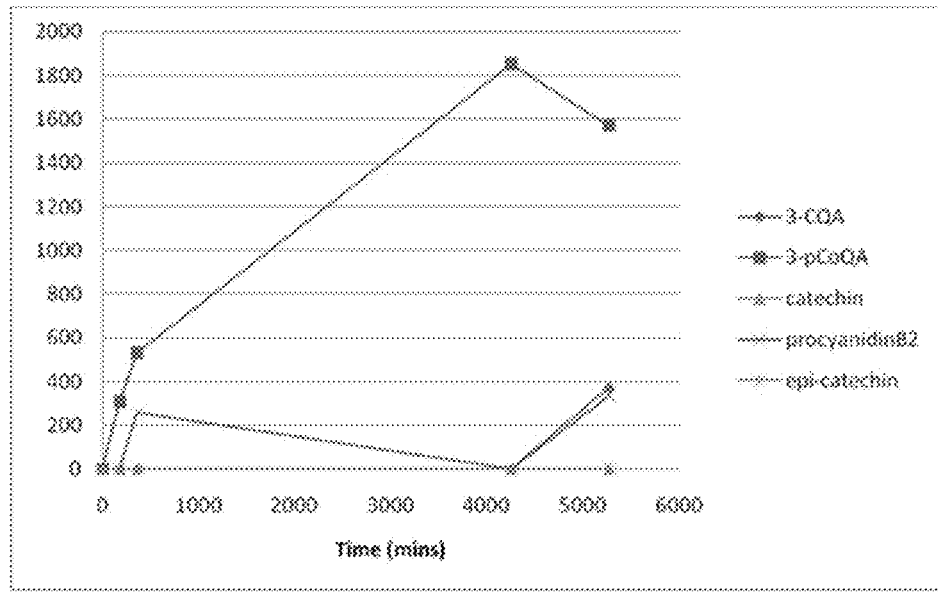
FIG. 3 is a graph showing the release of individual phenolic active agents 3-CQA (♦), 3-pCoQA (■), catechin (▲), procyanidinB2 (X), and epi-catechin (*) from PA-6 matrix as described in Example 3.

The observed kinetics of release of the individual phenolic active agents 3-pCoQA (♦), catechin (■), procyanidinB2 (▲), and epi-catechin (X) from the PVOH nanofibre is shown in FIG. 2. The observed kinetics of release of the phenolic active agents 3-CQA (♦), 3-pCoQA (■), catechin (▲), procyanidinB2 (X), and epi-catechin (*) from PA-6 matrix is shown in FIG. 3. As can be seen, the release of these phenolic compounds from each matrix varies significantly.

Figure 4:
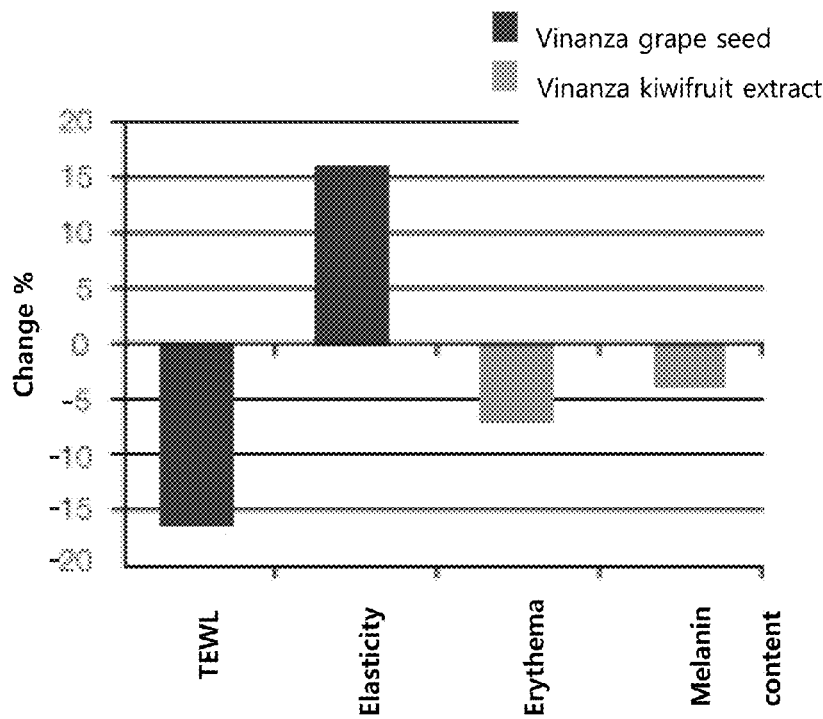
FIG. 4 is a graph showing the effect of Vinanza™ skin performance plus blend applied as a cream on skin performance.

Shown in FIG. 4 is the effect of Vinanza™ Grape Seed Extract on (1) trans epidermal water loss and (2) skin elasticity, and the effect of Vinanza™ Kiwifruit Extract on (1) skin redness, and (2) skin melanin content.

As can be seen in FIG. 4, Vinanza™ Grape Seed Extract improved skin cell integrity by decreasing trans epidermal water loss (TEWL) by at least 16%, and improved skin elasticity by 15%. Also demonstrated is that Vinanza™ Kiwifruit Extract decreased skin redness by 7% and lightened skin by 3.5%.

Figure 5:
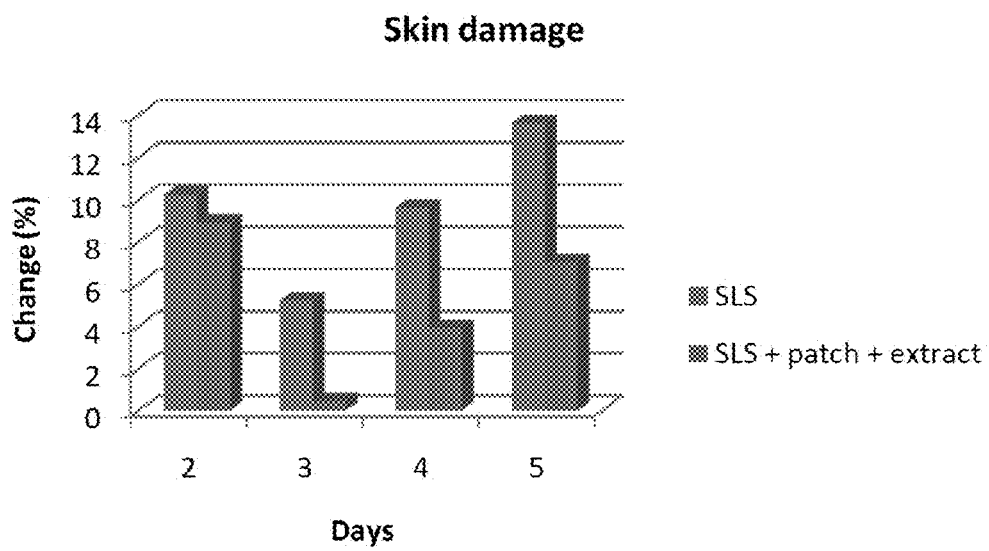
FIG. 5 is a graph showing the effect of Vinanza™ skin repair plus blend applied as a PVOH nanofibre patch on damaged skin.

Shown in FIG. 5 is Vinanza™ Skin Repair Plus applied as a PVOH nanofibres on the repair of skin damaged by the application of sodium lauryl sulphate (SLS). Here, the percent change was the difference between the marker of skin damage on the damaged skin, versus the same marker on undamaged skin, where a lower % change represents less damage.

As can clearly be seen in FIG. 5, the application of a patch comprising a nanofibre matrix of the invention, in this case comprising Vinanza™ Skin Repair Plus extracts, was very effective in minimising skin damage and speeding skin repair.

Example 4: Wound Healing Matrix

This example describes the preparation and use of a skin patch for assisting or enhancing wound healing.

Blackcurrant and Red grape extracts comprising active agents including one or more antimicrobial agents, and collagen (as described above in Example 1) are obtained. The extracts comprising one or more antimicrobial active agents and the collagen polymer are then mixed in a solvent phase.

Separately, grape seed extract comprising one or more skin repair active agents and PA-6 polymer are mixed in a solvent phase.

Once prepared, the polymer-active agent solutions are electro spun. The electro spinning produces a matrix of nanofibres, wherein the matrix comprises both collagen (water-soluble) and PA-6 (effectively water-insoluble) polymers.

The matrix of nanofibres is applied directly to a support, such as a woven bandage or patch, suitable for application. In this case, the electro spinning is performed directly onto the bandage or wound dressing.

The dressing is then packaged for storage prior to application to a wound. On application, a subset of the nanofibres, typically some or all of the water soluble nanofibres solubilise quickly to essentially immediately deliver one or more of the antimicrobial active agents and the collagen to the wound. Release of the active agents effective for skin repair from the PA-6 polymer then occurs over a longer time period, typically over several days.

Example 5: Skin Repair

This example describes the use of a skin patch for assisting or enhancing skin repair.

Grape seed extracts comprising active agents including one or more skin repair active agents, and collagen (as described above in Example 1) are obtained. The grape seed extract and the collagen polymer are then mixed in a solvent phase. Separately, the grape seed extract and PA-6 polymer are mixed in a solvent phase.

Once prepared, the polymer-active agent solutions are electro spun. The electro spinning produces a matrix of nanofibres, wherein the matrix comprises both water-soluble and water-insoluble polymers.

The matrix of nanofibres is applied directly to a support, such as a woven bandage or patch. In this example, the electro spinning is performed directly onto a patch.

The patch is then packaged for storage prior to application to damaged or sunburned skin. On application to skin, a subset of the nanofibres, typically some or all of the collagen nanofibres solubilise quickly to essentially immediately deliver one or more of the active agents present in the grape seed extract and the collagen to the skin for immediate effect. Release of additional active agents from the PA-6 polymer then occurs over a longer time period, from one hour to several days, thereby maintaining enhanced skin repair for the duration of application of the patch.

Example 6: Anti-Inflammatory

This example describes the preparation and use of a skin patch to promote anti-inflammatory effects at a skin site.

A honey extract derived through a water or ethanol extraction is produced. The honey extract contains a variety of phenolic and flavonoid compounds useful as anti-inflammatory agents. A collagen (as described above in Example 1) raw material is produced. The extract and collagen materials are then mixed in a solvent phase.

Once prepared, the polymer-active agent solutions are electro spun. The electro spinning produces a matrix of nanofibres with the honey derived actives associated with or chemically bound to the nanofibres.

The matrix of nanofibres may then be applied directly to a support, such as a woven bandage or patch, suitable for application. In this case, the electro spinning is performed directly onto the bandage or wound dressing.

The dressing is then packaged for storage prior to application to an inflamed skin site such as a wound. On application, the nanofibres solubilise quickly to immediately deliver one or more of the anti-inflammatory active agents and the collagen to the wound.

Example 7: Dual Enzyme and Bioactive Delivery

Enzymes may be used to activate or catalyse conversion of an inactive compound to an active compound on topical administration as well via other methods of administration. In this example, the enzyme myrosinase is incorporated into the nanofibres for use on application as a catalyst to convert glucosinolates into active ingredients such as sulforaphane.

Purified myrosinase enzyme is selected along with a suitable polymer such as those described above. The two are mixed in a solvent phase and electro spun being careful to avoid excessive process temperatures. The product resulting is myrosinase enzyme associated with the nanofibre and remains shelf stable in the absence of moisture.

In use, a precursor glucosinolate containing compound or compounds such as a broccoli extract may be applied to a skin surface for example in a cream or via a separate nanofibre based composition with glucosinolate associated therein. Myrosinase enzyme is released onto the skin/glucosinolate layer by moistening the nanofibre and applying it to the skin surface. The result is conversion of inactive glucosinolates to the active sulforaphane directly at the administration site thereby allowing a known and controlled delivery of active agent to the skin.

The above dual delivery concept may also be integrated into a single dressing using multilayers of nanofibres. A dual layer nanofibre matrix may be electro spun, a first skin contacting layer of nanofibres containing glucosinolates and a second layer on the first layer containing the myrosinase enzyme. Typically a mixture of these two compounds result in conversion of the stable glucosinolate to unstable sulforaphane that is undesirable during storage or manufacture. This is why for example, cream embodiments are not possible. The above described matrix keeps the active agents segregated during manufacture and storage thus preventing unwanted reactions. On delivery the nanofibres dissolve allowing the agents to mix and react. The speed of release can be tailored by using different nanofibre raw materials thereby for example causing rapid release of glucosinolates to the skin surface from the first layer and slightly slower release of the myrosinase from the second layer.

Example 8: Antioxidant Delivery

This example describes the preparation and use of a skin patch to deliver anti-oxidants to a skin site.

An olive leaf extract derived through a water or ethanol extraction is produced. The olive leaf extract contains a variety of flavonoid compounds including oleuropein and hydroxytyrosol useful as antioxidant agents. A collagen (as described above in Example 1) raw material is produced. The extract and collagen materials are then mixed in a solvent phase.

Once prepared, the polymer-active agent solutions are electro spun. The electro spinning produces a matrix of nanofibres with the olive leaf derived actives associated with or chemically bound to the nanofibres.

The matrix of nanofibres may then be applied directly to a support, such as a woven bandage or patch, suitable for application. In this case, the electro spinning is performed directly onto the bandage or wound dressing.

The dressing is then packaged for storage prior to application to a skin site. On application, the nanofibres solubilise quickly to immediately deliver the antioxidant active agents and the collagen to the wound.

Example 9: Antioxidant Delivery

This example describes the preparation and use of a skin patch to deliver anti-oxidants to a skin site.

A propolis extract derived through a water or ethanol extraction is produced. The propolis extract contains a variety of flavonoid compounds useful as antioxidant agents. A collagen (as described above in Example 1) raw material is produced. The extract and collagen materials are then mixed in a solvent phase.

Once prepared, the polymer-active agent solutions are electro spun. The electro spinning produces a matrix of nanofibres with the propolis derived actives associated with or chemically bound to the nanofibres.

The matrix of nanofibres may then be applied directly to a support, such as a woven bandage or patch, suitable for application. In this case, the electro spinning is performed directly onto the bandage or wound dressing.

The dressing is then packaged for storage prior to application to a skin site. On application, the nanofibres solubilise quickly to immediately deliver the antioxidant active agents and the collagen to the wound.

Example 10: Dual Enzyme and Phenolic Delivery

This example describes the preparation and use of a skin patch to deliver both enzymes and phenolics to a skin site.

A royal jelly extract is produced. Royal jelly produced in a hive contains a variety of phenolic compounds useful as active agents. Royal jelly also includes several enzymes including royalisin, apalbumin and apisimin. A collagen (as described above in Example 1) raw material is produced. The royal jelly and collagen materials are then mixed in a solvent phase.

Once prepared, the polymer-active agent solutions are electro spun. The electro spinning produces a matrix of nanofibres with the royal jelly derived actives associated with or chemically bound to the nanofibres.

The matrix of nanofibres may then be applied directly to a support, such as a woven bandage or patch, suitable for application. In this case, the electro spinning is performed directly onto the bandage or wound dressing.

The dressing is then packaged for storage prior to application to a skin site. On application, the nanofibres solubilise quickly to immediately deliver the antioxidant active agents and the collagen to the wound.

Example 11: Stability

The effects of storage and active stability were investigated.

Method: actiVLayr™ patches produced by New Zealand Extracts™ Limited were produced being a collagen based nanofibre with antioxidant actives (being Vinanza™) bonded and/or associated with the nanofibres. The nanofibres are spun onto a polypropylene backing.

The actiVLar™ product was stored in sealed foil sachets in a temperature controlled incubator at 45° C. and a RH of 95% to replicate accelerated gaining conditions. The condition of the patches was recorded after 14 and 28 days of storage and compared to patches that were stored in foil sachets at ambient room temperature and humidity.

Following recordal of the patch condition, the active agents were released by dissolving of the nanofibres in water and the resulting antioxidant capacity measured via ORAC activity was obtained and compared to the activity on day 0.

Figure 6:
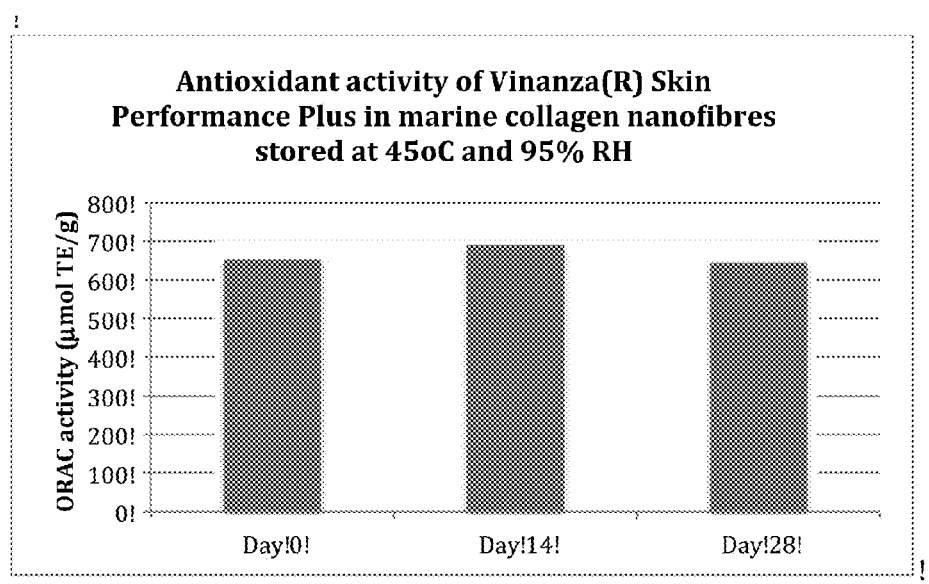
FIG. 6 is a graph showing the ORAC scores for samples stored under accelerated aging conditions.

Results: No visual changes to the patches were noticeable after either 14 or 28 days of storage indicating product stability under particularly trying conditions (accelerated aging). No substantial change in activity was noted for both the 14 and 28 day samples as shown in FIG. 6.

INDUSTRIAL APPLICABILITY

The nanofibre and bioactive compositions and their usage described herein provide bioactives, and methods of using these bioactives, for example in the treatment and prevention of skin diseases or conditions, and as such is expected to provide both social and economic benefits.

What is claimed is:
1. A composition comprising:
at least one nanofibre; and
an effective amount of at least one bioactive compound;
wherein the nanofibres are formed from a base material that is solubilised with the at least one bioactive compound in an aqueous based solvent solution and the base material and the at least one bioactive compound are together spun via electrospinning to form dry fibres;
wherein the at least one bioactive compound is chemically bonded to the nanofibres and the at least one bioactive compound remains stable during storage of the composition under ambient conditions substantially free of moisture; and, on exposure to moisture, the nanofibres are able to dissolve rapidly, thereby substantially releasing all of the at least one bioactive compound within about 5 minutes; and wherein the concentration of the at least one bioactive compound on the nanofibers is from approximately 0.1 to 30 g/m$^2$.

2. The composition as claimed in claim 1 wherein the at least one bioactive compound is stable for at least 8 days when stored at 20° C. in the absence of moisture.

3. The composition as claimed in claim 1 wherein the at least one bioactive compound is covalently bonded to the nanofibres.

4. The composition as claimed in claim 1 wherein the at least one bioactive compound is selected from the group consisting of: compounds that have at least one phenolic moiety; enzymes including a polypeptide with one or more tyrosine residues; and combinations thereof.

5. The composition as claimed in claim 1 wherein the at least one bioactive compound is selected from the following plants, parts thereof or extracts thereof: grape seed, kiwifruit, blackcurrant, boysenberries, red grape, broccoli, broccoli sprout, olive leaf, seaweed, pine bark, honey, propolis, royal jelly, or combinations thereof.

6. The composition as claimed in claim 1 wherein the at least one bioactive compound comprises approximately 10 to 80% by weight of the composition.

7. The composition as claimed in claim 1 wherein the nanofibres are manufactured from a polymer selected from the group consisting of: polyvinyl alcohol (PVOH), polyvinyl alcohol (PVA), polyamide 6 (PA-6), polyvinyl butyral (PVB), polyamide 6,6 (PA-6,6), polyethylene terephthalate (PET), polybutylene terephthalate (PBT), polylactic acid (PLA), poly(lactic-co-glycolic) acid (PLGA), polycaprolactone (PCL), nylon, alginate, cellulose, cellulose derivatives including cellulose acetate and carboxymethyl cellulose (CMC), gelatine, gelatin, chitosan, carrageenan, xanthan gum, zein, polysaccharides, polyhydroxyalkanoates (PHA), polyhydroxybutyrate (PHB), poly(3-hydroxybutyrate-co-3-hydroxyvalerate) (PHBV), and combinations thereof.

8. The composition as claimed in claim 1 wherein the nanofibres are formed from collagen protein.

9. The composition as claimed in claim 8 wherein the collagen protein is denatured to remove its helical structure and form whole chains (alpha chains) prior to electrospinning.

10. The composition as claimed in claim 8 wherein the collagen is derived from a marine source.

11. The composition as claimed in claim 1 wherein the solvent solution further comprises at least one organic acid compound and/or at least one alcohol compound.

12. The composition as claimed in claim 11 wherein the organic acid is selected from the group consisting of: citric acid, acetic acid, formic acid, carbonic acid, and combinations thereof.

13. The composition as claimed in claim 11 wherein the alcohol is selected from the group consisting of: ethanol, benzyl alcohol, isopropanol, and combinations thereof.

14. The composition as claimed in claim 11 wherein the organic acid and/or alcohol comprises less than approximately 20% of the solvent solution.

15. The composition as claimed in claim 1 wherein the nanofibre diameter ranges from approximately 10 to 1000 nm.

16. The composition as claimed in claim 1 wherein the composition is spun onto a substrate.

17. A multilayered matrix comprising a plurality of layers, each layer comprising the composition as claimed in claim 1, wherein;
(a) the at least one bioactive compound in at least one layer is segregated from at least one bioactive compounds in at least one other layer during storage preventing any reactions between the bioactive compounds in each layer during storage; and,
(b) on exposure to moisture, the nanofibres dissolve and the bioactive compounds in the different layers mix and react together.

18. The multilayered matrix as claimed in claim 17 wherein at least one layer is made from a nanofibre material that dissolves at a different rate to a second or further layer, thereby releasing the bioactive compounds at different rates.

19. A method of applying at least one bioactive compound topically to a subject to treat the skin of the subject, the method comprising the steps of:
(a) selecting a composition as claimed in claim 1;
(b) moistening the composition; and
(c) applying the composition topically to the skin of the subject.

20. The method as claimed in claim 19, wherein the treatment is selected from the group consisting of: promoting skin care or skin repair; assisting or enhancing wound healing; addressing a microbial infection; treating or preventing inflammation; promoting or enhancing cell proliferation; preserving or improving skin elasticity; preserving or improving skin moisture retention; lightening and/or whitening skin colour; delivering at least one antioxidant to skin; and combinations thereof.

21. A cosmetic skincare product comprising the composition as claimed in claim 1, wherein the product is in the form of: a plaster, a bandage, a dressing, a facial mask, a facial strip, a cosmetic patch, or any combination thereof.

22. A method of producing a composition as claimed in claim 1 by the steps of:
(a) selecting at least one bioactive compound;
(b) selecting at least one nanofibre base material;
(c) mixing the at least one bioactive compound and the at least one nanofibre base material with water to form an aqueous solution; and
(d) electro spinning the solution to form one or more nanofibres chemically bonded with the at least one bioactive compound.

23. The method as claimed in claim 22 wherein the conductivity of the solution is from approximately 1 to 5 mS/cm.

24. The method as claimed in claim 22 wherein the surface tension of the solution is from approximately 50 to 500 mN/m.

25. The method as claimed in claim 22 wherein the viscosity of the solution is approximately 250 to 2000 cSt.

* * * * *